United States Patent
Denisov

(10) Patent No.: US 9,150,909 B2
(45) Date of Patent: Oct. 6, 2015

(54) DETERMINATION OF THE INTEGRITY OF RNA

(75) Inventor: Vladimir Denisov, Santa Cruz, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 611 days.

(21) Appl. No.: 12/548,226

(22) Filed: Aug. 26, 2009

(65) Prior Publication Data
US 2010/0057371 A1  Mar. 4, 2010

Related U.S. Application Data

(60) Provisional application No. 61/093,060, filed on Aug. 29, 2008.

(51) Int. Cl.
*G01N 27/26* (2006.01)
*C12Q 1/68* (2006.01)
*G06F 19/00* (2011.01)

(52) U.S. Cl.
CPC .......... *C12Q 1/6816* (2013.01); *C12Q 1/6806* (2013.01); *C12Q 2545/113* (2013.01); *C12Q 2563/107* (2013.01); *C12Q 2565/125* (2013.01); *G01N 2333/4728* (2013.01); *G01N 2800/34* (2013.01)

(58) Field of Classification Search
CPC .............. C12Q 1/6806; C12Q 1/6816; C12Q 2545/113; C12Q 2563/107; C12Q 2565/125; C12Q 2561/12; C12Q 2539/101; G01N 2333/4728; G01N 2800/34
USPC ................... 702/19; 204/450, 600; 435/288.7
See application file for complete search history.

(56) References Cited

U.S. PATENT DOCUMENTS

| | | | |
|---|---|---|---|
| 7,267,948 B2* | 9/2007 | Vo-Dinh | 435/6.11 |
| 7,968,327 B2* | 6/2011 | McMaster et al. | 435/270 |
| 2006/0011862 A1* | 1/2006 | Bernstein | 250/461.2 |
| 2006/0246577 A1* | 11/2006 | Schroeder et al. | 435/288.7 |
| 2008/0050746 A1 | 2/2008 | McMaster et al. | |

(Continued)

FOREIGN PATENT DOCUMENTS

| DE | 103 15 581 | 11/2004 |
|---|---|---|
| JP | 2007-256979 | 9/2007 |

OTHER PUBLICATIONS

Vivien Marx, "RNA Quality: Defining the Good, the Bad, & the Ugly", Oct. 26, 2006, 6 pp, http://www.gene-quantification.com/good-bad-ugly.pdf.*

(Continued)

*Primary Examiner* — Alexander Satanovsky
(74) *Attorney, Agent, or Firm* — Kilpatrick Townsend & Stockton LLP

(57) ABSTRACT

Methods, systems, and apparatus make a determination of a level of integrity of a sample of biomolecules. For example, the determination of the integrity of RNA in a sample may be done in a fast and reproducible manner, such that the user can be assured of accuracy of a test (e.g. quantitative polymerase chain reaction qPCR) on the sample and compare results of different samples. The determination of integrity of an RNA sample is performed by comparing a size profile to reference size profiles (degradation standards) obtained from degradation over different lengths of times. As the reference scale of the level of integrity is derived from the actual degradation that occurs in a sample, high accuracy, reproducibility, and efficiency is provided.

22 Claims, 13 Drawing Sheets

(56) References Cited

U.S. PATENT DOCUMENTS

2008/0103296 A1* 5/2008 Zhao et al. .................. 536/22.1
2010/0105872 A1* 4/2010 De Sadelleer et al. ........ 530/375
2010/0298154 A1* 11/2010 Simmet et al. .................. 506/7

OTHER PUBLICATIONS

Fleige et al.; "RNA integrity and the effect on the real-time qRT-PCR performance." *Molecular Aspects of Medicine*; 27: 126-139 (2006).
Schroeder et al.; "The RIN: an RNA integrity number for assigning integrity values to RNA measurements." *BMC Molecular Biology*; 7(3), Jan. 31, 2006. (epub, 14 pages).
International Search Report and Written Opinion dated Oct. 22, 2009 for PCT/US2009/055497 (9 pages).
Mueller, O., et al., "RNA Integrity Number (RIN)—Standardization of RNA Quality Control," Application Note Technologies, May 1, 2004, 8 pages.
Auer, H., et al., "Chipping away at the chip bias: RNA degradation in microarray analysis," Nature Genetics, vol. 35, No. 4, Dec. 1, 2003, pp. 292-293.
Fontanesi, L., et al., "Evaluation of post mortem stability of porcine skeletal muscle RNA," Meat Science, vol. 80, No. 4, Dec. 1, 2008, pp. 1345-1351.
Pfaffl, et al., "RNA integrity and the effect of the real-time qRT-PCR performance," Molecular Aspects of Medicine, 2006, vol. 27, pp. 126-139.
Supplementary European Search Report mailed Mar. 23, 2012 in European Application No. EP09810713, 7 pages.
European Office Action issued on Jan. 11, 2013 in European Patent Application No. 09810713, 4 pages.
Notice of Rejection mailed on May 21, 2013 in Japanese Patent Application No. 2011-525270, with English translation, 8 pages.
Non-Final Notice of Rejection mailed on Mar. 11, 2014 in Japanese patent Application No. 2011-525270, with English translation, 4 pages.
Official Communication dated Sep. 4, 2014 for European Patent Application No. 09810713.9, 3 pages.
Decision for Grant dated Aug. 19, 2014 for Japanese Patent Application No. 2011-525270, with partial translation, 4 pages.

* cited by examiner

| Well ID | Sample Name | RNA Area | RNA Concentration (ng/µl) | Ratio [28S/18S] | RQI | RQI Classification | RQI Alert |
|---|---|---|---|---|---|---|---|
| L | Ladder | 425.40 | 160.00 | | | | |
| 1 | Sample 1 | 325.68 | 122.49 | 1.80 | 10.0 | ■ | |
| 2 | Sample 2 | 360.16 | 135.46 | 1.03 | 9.2 | ■ | |
| 3 | Sample 3 | 365.87 | 137.61 | 0.99 | 8.4 | ■ | |
| 4 | Sample 4 | 385.68 | 145.06 | 0.79 | 7.5 | ■ | |
| 5 | Sample 5 | 388.73 | 146.21 | 0.55 | 6.7 | ■ | |
| 6 | Sample 6 | 407.10 | 153.12 | 0.45 | 5.9 | ■ | |
| 7 | Sample 7 | 387.23 | 145.64 | 0.22 | 5.1 | ■ | |
| 8 | Sample 8 | 370.38 | 139.31 | 0.11 | 4.3 | ■ | |
| 9 | Sample 9 | 375.31 | 141.16 | 0.05 | 3.5 | ■ | |
| 10 | Sample 10 | 375.76 | 141.33 | 0.01 | 2.6 | ■ | |
| 11 | Sample 11 | 362.32 | 136.28 | 0.00 | 1.8 | ■ | |
| 12 | Sample 12 | 457.51 | 172.08 | 0.35 | 1.0 | ■ | |

FIG. 4A

| From [#] | To [#] | Color |
|---|---|---|
| 1 | 4 | |
| 4 | 7 | |
| 7 | 10 | |

FIG. 4B

Table 1. Reproducibility of RQI measurements of intact and partially degraded RNA samples.*

| RNA Quality | Experion RNA Analysis Kit | Quantity, ng/µl | Number Samples | Average RQI | Range | SD | %CV |
|---|---|---|---|---|---|---|---|
| Intact | StdSens | 250 | 72 | 9.4 | 8.7–9.7 | 0.33 | 3.5 |
| Less intact | StdSens | 100 | 12 | 6.6 | 6.4–6.8 | 0.14 | 2.1 |
| Less intact | HighSens | 2 | 11 | 6.0 | 5.6–6.2 | 0.17 | 2.9 |

* RNA isolated using the Bio-Rad's Aurum™ total RNA fatty and fibrous tissue kit.

FIG. 9A

Table 2. Lower limits of RNA concentrations for RNA detection and RQI determination.

| Experion RNA Analysis Kit | Qualitative LLOD* of RNA | Lower Limit for RQI Determination | Quantitative LLOD of RNA |
|---|---|---|---|
| StdSens | 5 ng/µl | ≥10 ng/µl | 25 ng/µl |
| HighSens | 100 pg/µl | ≥200 pg/µl | 200 pg/µl |

* Lower limit of detection.

FIG. 9B

Table 3  Impact of RNA degradation on real-time qPCR $C_T$.*

| Incubation time (hr) | RQI | 18S rRNA | β-Actin | GAPDH | HPRT | β-Tubulin |
|---|---|---|---|---|---|---|
| 0 | 9.9 | 11.2 | 16.5 | 18.1 | 22.5 | 19.7 |
| 1 | 6.9 | 11.6 | 18.2 | 20.5 | 25.1 | 20.9 |
| 3 | 3.5 | 12.0 | 20.1 | 22.9 | 27.9 | 22.7 |
| 5 | 1.8 | 12.1 | 22.0 | 26.1 | 29.5 | 24.6 |
| 7 | 1.5 | 12.5 | 23.5 | 28.0 | 30.3 | 26.5 |
| $\Delta C_T$ | | 1.3 | 7.0 | 9.9 | 7.8 | 6.8 |

FIG. 9C

DETERMINATION OF THE INTEGRITY OF RNA

CROSS-REFERENCES TO RELATED APPLICATIONS

The present application claims priority from and is a nonprovisional application of U.S. Provisional Application No. 61/093,060, entitled "RNA Quality Factor" filed Aug. 29, 2008, the entire contents of which are herein incorporated by reference for all purposes.

BACKGROUND

This invention generally relates to electrophoresis systems, and more particularly to using an electrophoresis system to determine an integrity of the biomolecules in a sample.

Gene expression analysis is essential to an understanding of molecular processes involved in health and disease. The ability to accurately quantitate steady-state levels of RNA is critical for studying molecular mechanisms of gene expression regulation. RNA quantitation techniques (such as northern blots, DNA microarrays, and real-time quantitative PCR) rely on the use of not only pure, but also intact RNA (i.e. RNA of high integrity). High-throughput gene expression analysis requires rapid, reliable, and standardized evaluation of RNA integrity. Yet, the methods to accurately and objectively evaluate the integrity of RNA molecules, prior to embarking on time-consuming, labor intensive, and costly projects, are limited.

Spectrophotometric methods to evaluate RNA concentrations and purity are well established and widely used. Absorbance at 260 nm (A260) gives an accurate measure of RNA concentration, and the ratio A260/A280 is an accepted indicator of the purity of an RNA preparation with respect to protein or phenol contaminations. However, these methods by themselves may give misleading results because they do not give any information on DNA contamination, the degradation state, or integrity of the sample. While RNA concentration and quality are important parameters for successful downstream applications, RNA integrity is of utmost importance when applications involve RNA quantitation for gene expression studies such as quantitative real-time RT-PCR and cDNA microarrays. Using partially degraded RNA from various states of degradation will lead to varying and incorrect quantitation results, both in microarray experiments and real-time PCR experiments.

The traditional method for assessing the integrity of an RNA sample is by visual inspection after electrophoresis on a formaldehyde agarose gel in the presence of a fluorescent dye (or other luminescent agent), such as ethidium bromide. Observation of two sharp bands, one each for the large and small subunit ribosomal RNAs (rRNAs), with the intensity of the larger band being about twice that of the smaller band, is indicative of intact RNA. While this method is relatively quick and inexpensive, interpretation of the data requires a fair amount of experience, and is still prone to inconsistencies.

Another limitation of this technique using a formaldehyde agarose gel is a requirement of on the order of 200 nanograms (ng) of RNA to make an accurate assessment of its integrity. However, when RNAs are extracted from tissues (such as biopsies) that are available in very limited quantities, agarose gel analysis may not be possible.

A major improvement in RNA analysis occurred with the introduction of microfluidics-based electrophoresis systems that require as little as 100 pg of RNA to produce an electropherogram displaying two distinctive peaks of rRNAs. The digital data composing the electropherogram can be used for a series of computer-based analyses. For example, RNA integrity can be evaluated and quantitated automatically by comparing the area of the peaks corresponding to the rRNAs. In theory, a 28S/18S rRNA ratio close to 2 should be indicative of intact RNA. However, in reality, the rRNA ratio may not be very reliable, e.g., because the peak area measurements are dependent on the chosen start and end points of the peaks.

Because of the limited utility of and reproducibility of rRNA ratios to assess RNA integrity, an existing method (Schroeder et al. US 2006/0246577) attempts to provide a standardized scale for determining RNA integrity. This method obtains a very large number of electropherograms and has trained experts assign a RNA integrity number (RIN). A neural network then determines the features (8 total) of an electropherogram that correspond to certain RIN values. This method can take quite a long time to prepare, e.g., due to the very large number of electropherograms required, the need for evaluation by trained experts, and the computational demands of the neural network. Additionally, this method can provide inaccuracies (inconsistencies) for the researcher, e.g., due to variances in the expert-assigned numbers and varied samples used.

Therefore, it is desirable to have improved methods for determining an integrity of a sample of RNA or other biomolecules.

BRIEF SUMMARY

Embodiments of the invention make a determination of a level of integrity of a sample of biomolecules. For example, the determination of the integrity of RNA in a sample may be done in a fast and reproducible manner, such that the user can be assured of accuracy of a test (e.g. quantitative polymerase chain reaction qPCR) on the sample and compare results of different samples. The determination of integrity of an RNA sample is performed by comparing a size profile to reference size profiles (degradation standards). As the reference scale of the level of integrity is derived from the actual degradation that occurs in a sample, embodiments provide high accuracy, reproducibility, and efficiency in creating the standards. In one aspect, embodiments provide a high-throughput method of determining RNA degradation, which may be implemented in data analysis by a computer system.

According to one exemplary embodiment, a method of determining a level of integrity of a sample of biomolecules is provided. A first size profile of the sample of biomolecules is received, where the size profile provides a measure of a distribution of values of at least one dimension of the biomolecules in the sample. A computing device compares the first size profile to a plurality of reference size profiles. Each reference size profile is measured at a different time of degradation of a reference sample of biomolecules, and each reference size profile correlates to a different level of integrity. Based on a similarity of the first size profile to one or more of the reference size profiles, the computing device determines the level of integrity of the sample of biomolecules.

According to other exemplary embodiments, computer readable medium and electrophoresis systems that implement methods described herein are also provided.

According to another exemplary embodiment, a method of manufacturing an electrophoresis system is provided. At least one reference sample of biomolecules is received. A respective size profile of the reference sample of biomolecules is measured at each of a plurality of successive times of degradation of the reference sample. Each size profile is mapped to a level of integrity, where a size profile measured at a later time of degradation maps to a lower level of integrity. The size profiles may be stored in a computer readable medium of the electrophoresis system along with the corresponding levels of integrity for each size profile.

A better understanding of the nature and advantages of the present invention may be gained with reference to the following detailed description and the accompanying drawings.

BRIEF DESCRIPTION OF THE DRAWINGS

FIG. 4A shows a table 400 of a mapping of the reference size profiles 410 (each one at a different time) to a level of integrity (RQI 450) according to embodiments of the present invention.

FIG. 4B shows a table 490 that provides which size profiles (degradation standards) correspond to which color according to embodiments of the present invention.

FIG. 9A is a table illustrating the reproducibility of RQI measurements of intact and partially degraded RNA samples according to an embodiment of the present invention.

FIG. 9B is a table illustrating the lower limits of RNA concentrations for RNA detection and RQI determination according to an embodiment of the present invention.

FIG. 9C shows a table illustrating the impact of RNA degradation on real-time qPCR CT according to an embodiment of the present invention.

DETAILED DESCRIPTION

Before a scientist performs tests on a sample of biomolecules, the scientist would like to know whether the biomolecules are intact (i.e. have high integrity). For example, if the scientist is studying a certain type of RNA, the scientist wants to know whether the RNA have been broken (low integrity) or have survived the travel from the tissue to the sample holder.

There are different characteristics of a sample to determine whether the sample is suitable for performing the test. The concentration measures the amount of biomolecules (e.g. relative to a solvent, such as water) in the sample. If the concentration is low, the test may not have enough biomolecules to obtain any measurement.

The quality of the biomolecules relates to the biomolecules themselves, such as contamination. For example, if the sample includes different types of molecules (e.g. other molecules that are the same size as the biomolecules of interest), the sample may not have good quality when the scientist is only interested in one or a few of the biomolecules. The quality also includes the integrity of the biomolecules, which can be even more prevalent than contamination.

As used herein, the term "integrity" is a measure (extent) of a degradation of the biomolecules of a sample, e.g., relative to a starting point (such as when the biomolecules are in tissue). Over time, the biomolecules (e.g. RNA) may cleave and become smaller particles. This degradation can causes errors as the test may not detect the biomolecules because they have changed form (e.g. becoming smaller). Thus, in one aspect, a determination of integrity can test how similar the biomolecules of the sample are relative to the biomolecules when they are in living tissue. As used herein, a "biomolecule" is any molecule that has one state in a living organism and can degrade.

Since the size of a biomolecules is related to the integrity, the size may be used to measure the integrity. Electrophoreses techniques measure the size particles, and thus are well suited for such integrity measurements. Embodiments of the invention provide an accurate, efficient, and consistent way to measure the integrity of the biomolecules of a sample.

Figure 1A:
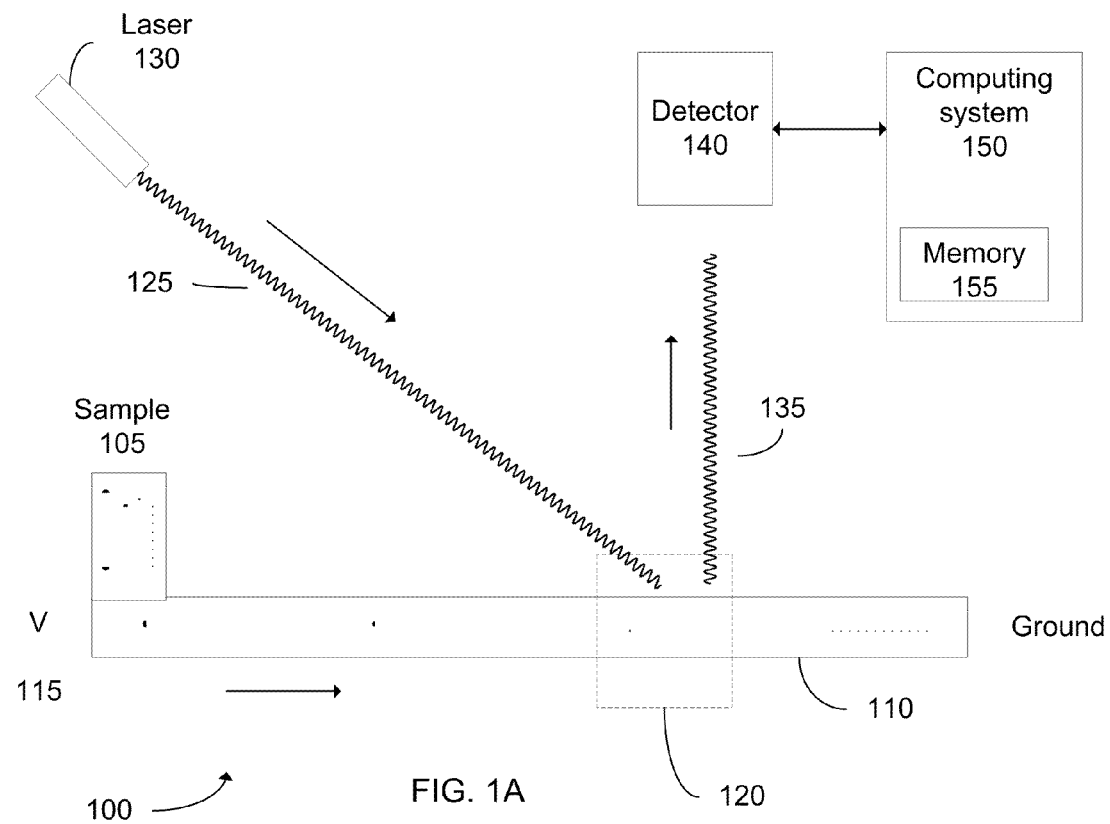
FIG. 1A shows an electrophoresis system 100 according to embodiments of the present invention.

FIG. 1A shows an electrophoresis system 100 according to embodiments of the present invention. As shown, the electrophoresis system 100 is microfluidics-based. However, other types of electrophoresis systems may be used in other embodiments. These methods, which measure fluorescence of a fluorophore bound to very small amounts of RNA, overcome many of the limitations of agarose gel electrophoresis. For example, as little as 100 pg of RNA may be needed to produce an electropherogram displaying two distinctive peaks of rRNAs.

In operation, the biomolecules of sample 105 is provided into at least one channel 110. The biomolecules of the sample 105 are driven through the channel 110 from left to right (motion depicted with an arrow) by the voltage (V) 115. Note that the voltage may be positive or negative. As shown, the biomolecules have different sizes, which is depicted as dots of different sizes. For example, some of the biomolecules (e.g. RNA) may have a first length and others have a second length that is longer than the first length.

Biomolecules of different lengths will travel at different speeds. Smaller molecules will be accelerated to higher speeds since they are easier to move with a same amount of force (i.e. the electrical force which may be about the same for each distinct molecule). This difference in speed can be used to determine the size of the biomolecules.

As the biomolecules move through the channel 110, they reach a detection region 120. Since the biomolecules of different size move at different speeds, they will reach the detection region 120 at different times. Once a biomolecule reaches the detection region 120, the biomolecule receives electromagnetic radiation 125 from a laser 130. The biomolecules have fluorescent dyes as a fluorescent intercalating agent.

When the radiation 125 is received by the biomolecules, the fluorescent agent is excited and emits its own electromagnetic radiation 135. Using ethidium bromide as the fluorescent dye can require on the order of 200 ng of RNA to make an accurate assessment of its integrity. The amount needed can be reduced by using alternative fluorescent dyes, e.g., to as little as 100 picograms (pg) of RNA.

Figure 1B:
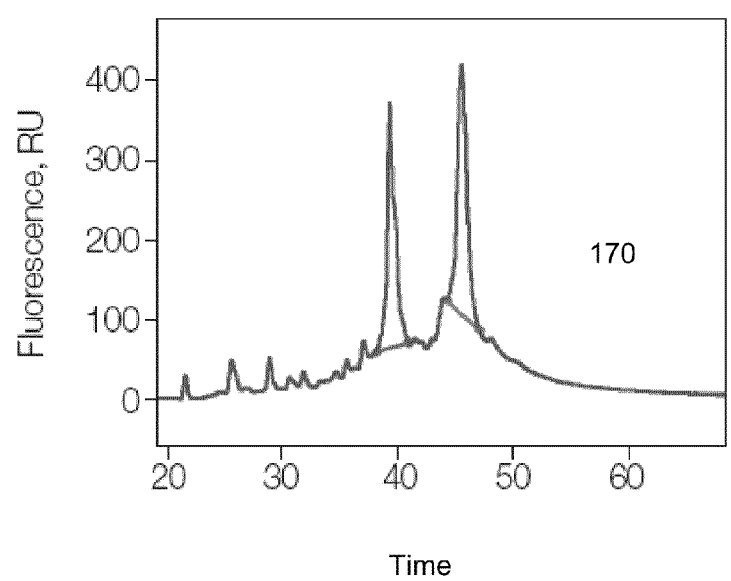
FIG. 1B shows an example of an electropherogram according to embodiments of the present invention.

A detector 140 receives the radiation 135 and measures the amount (strength) of the signal over time. The strength of the signal at a specific instant in time will depend upon the number of biomolecules present in the detection region 120 during that time. In this manner, the number of particles with a specific size can be measured by looking at a plot of the signal over time (an example of a size profile), which is called an electropherogram in some embodiments. A size profile provides a measure of a distribution of values of at least one dimension (e.g. length) of the biomolecules in the reference sample FIG. 1B shows an exemplary electropherogram trace 170 as an example of a size profile of a sample of biomolecules. The Y axis shows a strength of the fluorescent signal in relative units (RU). The X axis is time as measured in seconds. The electropherogram trace 170 provides the distribution of the size of the particles, with a higher RU value corresponding to more molecules of a particular size. The electropherogram trace 170 displays two distinctive peaks of rRNAs, which is normal for a sample having high integrity. Other sizes profiles, e.g., ones that show differences spatially as opposed to temporally, may also be used in embodiments of the present invention.

In one embodiment, after the detector 140 reads a specific value at an instant in time, the detector 140 can then send the one data point to a computing system 150. In another embodiment, after the detector 140 reads a whole trace, the detector 140 can then send the entire size profile to the computing system 150, which analyzes the size profile to determine a level of integrity. Accordingly, in one embodiment, the electrophoresis system 100 combines quantitation and quality assessment in a single apparatus. In one aspect, the level of integrity is determined by comparing the just measured size profile to reference size profiles stored in a memory 155.

In one embodiment, the method of determining the level of integrity is based on matching an RNA sample's size profile with the reference size profiles (e.g. by comparing electropherograms). Since the RNAs degrade and therefore decrease in size, eventually disappearing, there is an accumulation of fast-moving, low molecular weight components, while the amount of high molecular weight components is decreasing. In simple terms, the components migrate towards the left end of the electropherogram. It is therefore possible to establish a set of profile standards—from intact to degraded—constituting a degradation reference scale from 10 (intact) to 1 (fully degraded).

A description of the creation of the reference size profiles (also called degradation standards) follows.

Figure 2:
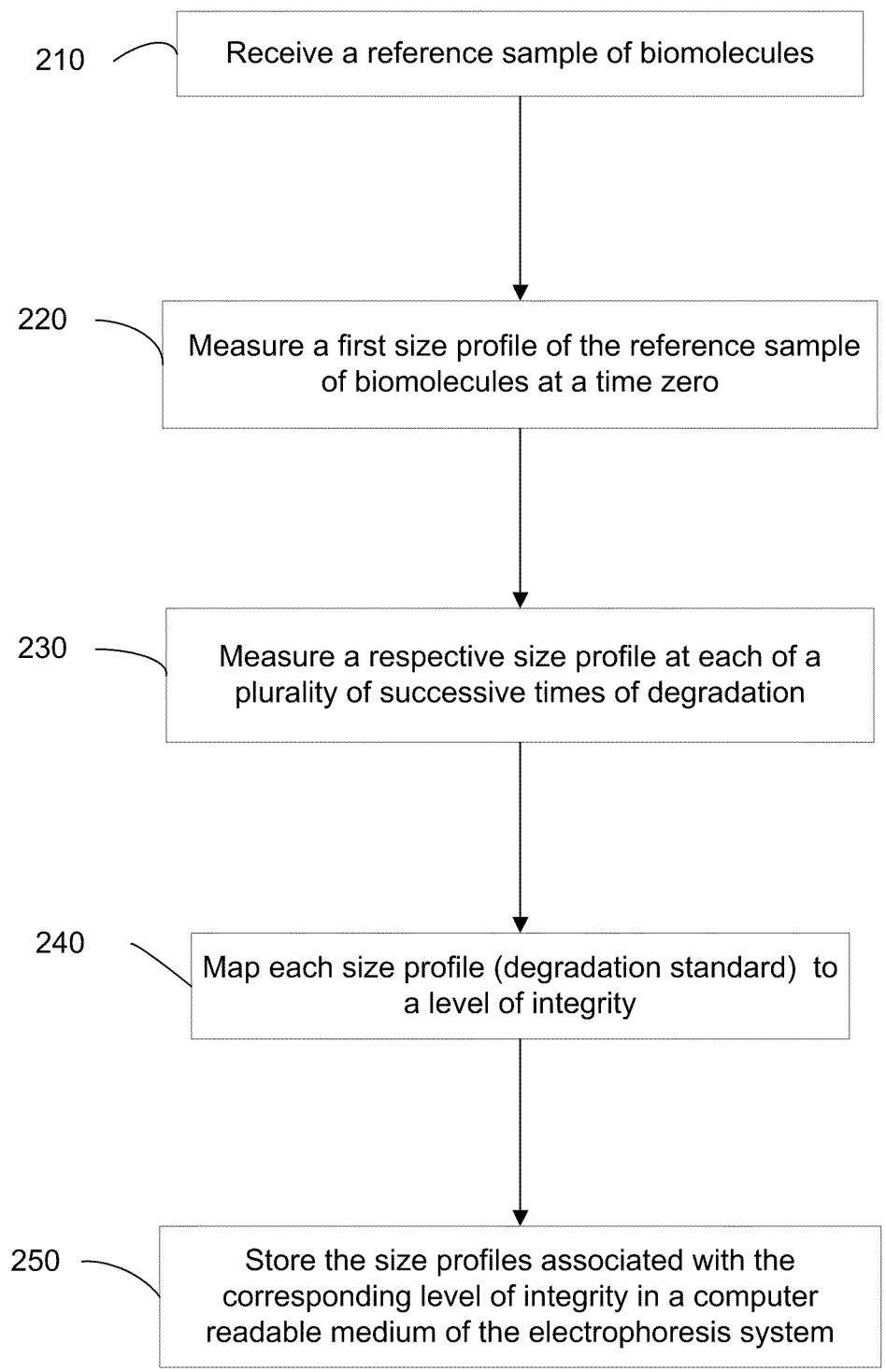
FIG. 2 is a flowchart illustrating a method 200 of manufacturing an electrophoresis system that determines a level of integrity of a sample according to embodiments of the present invention.

FIG. 2 is a flowchart illustrating a method 200 of manufacturing an electrophoresis system that determines a level of integrity of a sample according to embodiments of the present invention. The electrophoresis system (e.g. system 100) is capable of determining a level of integrity of a sample using reference size profiles (degradation standards) that are stored in the electrophoresis system.

In step 210, one or more reference samples of biomolecules is received. A reference sample may be composed of a plurality of separate vials or other containers. The sample may also be subsequently split up into the separate vials or other containers. However, each of the reference samples have the same or similar initial integrity. In one aspect, the degradation standards are generated from RNA of the same origin and the same concentration.

In step 220, a first size profile of the reference sample of biomolecules is measured at a time zero. The time zero is taken as the start of degradation, thus this first size profile is taken as having no degradation. In some embodiments, the sample may actually have no degradation relative to the tissue from which the sample was taken. In other embodiments, the sample may have some or minimal degradation.

In step 230, a respective size profile of the reference sample of biomolecules is measured at each of a plurality of successive times of degradation of the reference sample. In one embodiment, when the reference sample is initially split into several containers, each measurement may come from a different container.

The successive times may be widely varying, depending on the rate of degradation that is occurring. For example, the times may be periodic (e.g. every hour or ½ hour) or separated by different times (e.g. measured more often as the beginning relative to the end). Also, as different biomolecules may degrade at different rates, different sets of reference size profiles may be used depending on the biomolecules of interest. For example, in one embodiment, the times may be 0, 3, 5, 12, 20, 25, 31, 40, 52, 90, 150, and 270 min.

In one embodiment, the respective size profile referred to relate to the reference size profiles that are used in later steps. For example, many size profiles may be measured at varying times, but one some of these reference size profiles are considered part of the plurality obtained (kept) in step 230.

In step 240, each size profile is mapped to a level of integrity, wherein a size profile measured at a later time of degradation maps to a lower level of integrity. In one embodiment, the level of integrity is measured from 10 (intact, i.e. first size profile) to 1 (fully degraded). In another embodiment, the mapping is performed to a color scale. In yet other embodiments, a text based scale may be used.

In step 250, the size profiles associated with the corresponding level of integrity are stored in a computer readable medium (e.g. memory 155) of the electrophoresis system. In one embodiment, the standards may be stored as the run files in a separate folder and deployed along with the application during the software installation process of the electrophoresis system.

The size profile may be stored in any suitable form. In one embodiment, the size profile is a sequence of data points, each data point including time and the corresponding fluorescence value. In another embodiment, the size profile is a set of numerical values that describe the data points of the electropherogram, graph, stain, or other measure. For example, the size profile may be one or more ratios of different regions of the electropherogram, as described in more detail later.

In one embodiment, the degradation standards were generated by incubating 12 human liver RNA samples at a concentration of 100 ng/ul (Experion RNA StdSens analysis kit) in TE (10 mM Tris-HCl pH 8.0, 1 mM EDTA) at 90° C. Electropherograms of the standards are shown on the FIG. 3A.

Figures 3A, 3B:
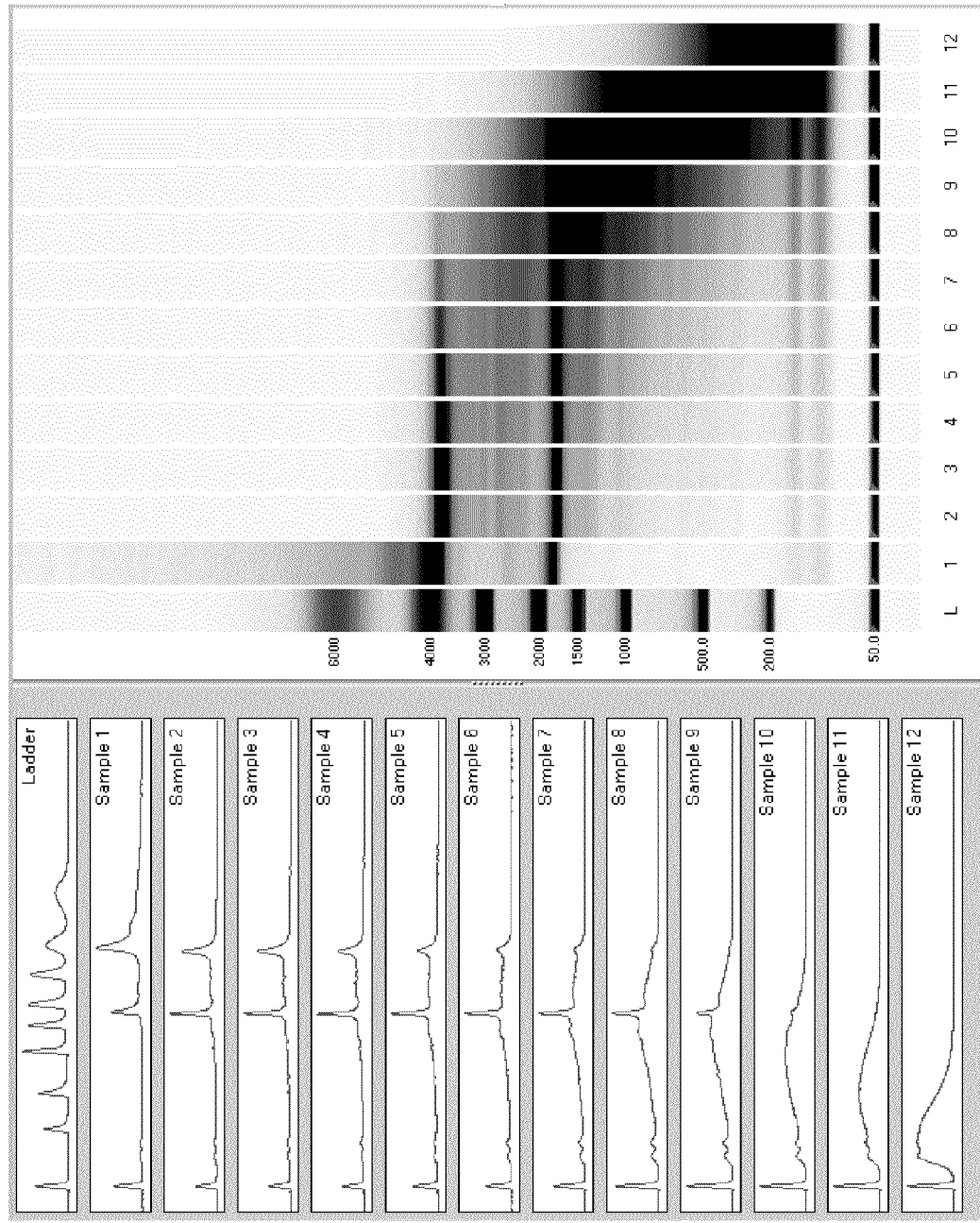
FIGS. 3A and 3B show different reference size profiles (marked as different sample numbers) taken at different times of degradation according to embodiments of the present invention.

FIGS. 3A and 3B show different reference size profiles (marked as different sample numbers) taken at different times of degradation according to embodiments of the present invention. FIG. 3A shows electropherograms for 12 RNA degradation standards. FIG. 3B shows virtual gel image of the 12 RNA degradation standards.

In FIG. 3B, L refers to the RNA ladder. A DNA ladder is a solution of DNA molecules of different lengths used in electrophoresis as a reference to estimate the size of unknown biomolecules.

In one aspect, the different standards show a regular progression of degradation over time. In other words, a significant (and sometimes equal) amount of degradation occurs between each sample. The times chosen of the sample may vary, depending on the rate of degradation that is occurring. The rate of degradation may vary based on an incubation temperature or other external conditions.

As one can see, the peaks for the sample 1 (no degradation) migrate to the left as time elapses. Such migration and change of peaks can be used to identify a level of integrity of the biomolecules of a sample. The level of integrity may be equal to or be composed of an RNA quality indicator RQI when the biomolecules are RNA.

FIG. 4A shows a table 400 of a mapping of the reference size profiles 410 (each one at a different time) to a level of integrity (RQI 450) according to embodiments of the present invention. The mapping may be linear or non-linear and have various forms. For example, if there were 10 standards, a linear mapping would provide each successive size profile having an RQI value 450 of one less than the previous size profile.

The RNA area 420, RNA concentration, ratio 440 of peak 28S to peak 18S, and RQI classification 460 are also provided. The RNA area 420 is the total area under the curve in the electropherogram and may be used to normalize certain features of the electropherogram traces, e.g., in order to account for spurious shifts up and down in the traces. For example, an area of one region relative to another region (such as ratio 440 of peak 28S to peak 18S, which is discussed later) may be normalized (e.g. divided) by the RNA total area 420.a In the example shown, 12 the size profiles (degradation standards) 410 are provided (e.g., the standards from FIG. 3A); however, any number of standards may be used. In one embodiment, the standards are linearly mapped to RQI 450 on the interval from 1 to 10, where 1 corresponds to the most degraded standard (sample 12) and 10 corresponds to the most intact standard (sample 1).

For a linear mapping of standard number to RQI 450, where the standards are taken at shorter time intervals at first and then larger time intervals later, the RQI value 450 decreases fast vs. time and then begins to level out at a low value (e.g. <2) for large times (e.g. greater than 1 hour). In one aspect, such a linear mapping when the time periods are not uniform may be used when the degradation between different standards corresponds to a same percentage of change in degradation. In such an example, more degradation (e.g., as measured by the ratio 440) would occur initially (10 to 9) then from (7 to 6), but a similar percentage may occur.

In other embodiments where the samples are taken at relatively equal times, the RQI value may decrease at the same speed over time. A non-linear decrease (e.g. fast at first) in RQI 450 vs. time would be more common at a higher temperature (e.g. 90° C.), whereas a more linear decrease might occur at room temperature (27° C.). However, in either case, the standards may correspond to roughly equal amounts of degradation.

The degradation standards 410 or the RQI 450 may also mapped to a RQI classification 460, which may be a simple color coded scheme to identify if a sample is good or not. Text based classifying schemes may also be used. The RQI classification 460 may be defined by the user, and also may correspond to a level of integrity.

FIG. 4B shows a table 490 that provides which size profiles (degradation standards) correspond to which color according to embodiments of the present invention. In one embodiment, relationships between the color scale and the reference size profile number or a numerical level of integrity (e.g. RQI 450), which may be normalized, are defined in the settings and can be changed by the user.

The RQI 450 (or equivalently RQI classification 460 as a result of a mapping) can be used as a standardized measure of RNA integrity across samples and experiments. It provides an objective and consistent criterion to select samples that meet minimal integrity levels required for specific downstream applications. The connection between RQI value and the utility of a sample for a specific downstream application has to be determined empirically by the user. Once this value is known, it can be used to specify the color code used in a run summary page, e.g., on a user interface of the computing system 150.

In some embodiments, the level of integrity is provided as the RNA quality indicator (RQI). The RQI can be used to measure RNA integrity by comparing the electropherogram of RNA samples to the series of standardized degraded RNA samples. As described above, a number between 10 (intact RNA) and 1 (highly degraded RNA) can be returned for each eukaryotic RNA sample run on an electrophoresis system.

Figure 5:
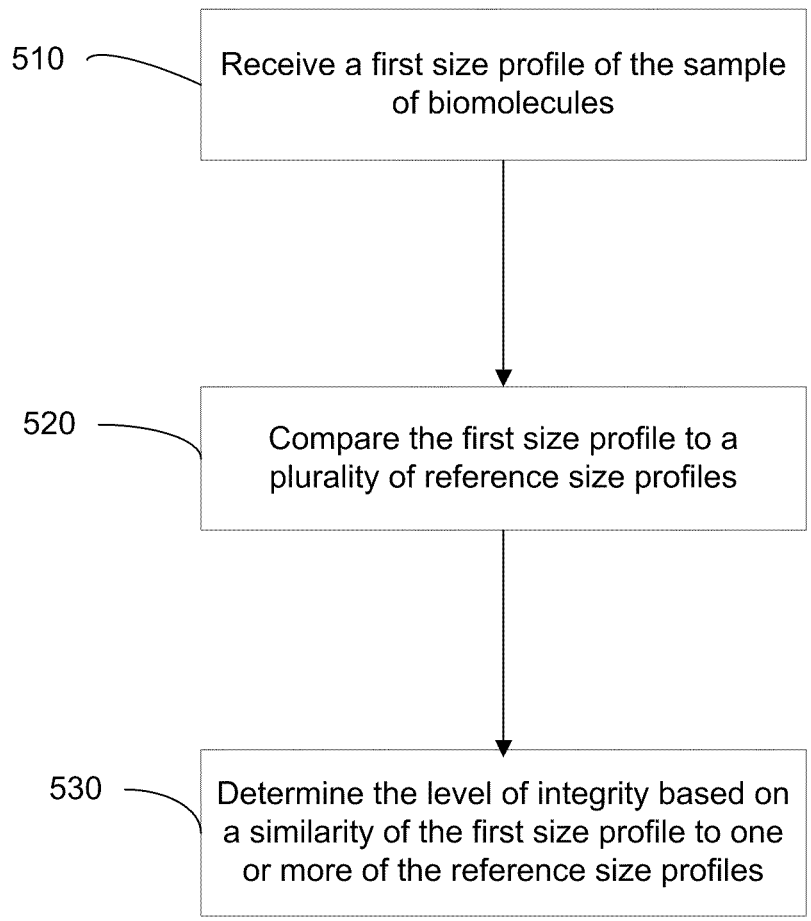
FIG. 5 is a flowchart of a method 500 for determining a level of integrity of a sample of biomolecules according to embodiments of the present invention

FIG. 5 is a flowchart of a method 500 for determining a level of integrity of a sample of biomolecules according to embodiments of the present invention. The sample of biomolecules is the sample for which it is desired to determine the level of integrity. In one embodiment, if the sample is contaminated (e.g. has a low quality due to other molecules), then the method 500 is aborted. In one aspect, the user can identify the quality by visual inspection of an output of an electrophoresis system.

In step 510, a first size profile of the sample of biomolecules is received. The size profile provides a measure of a distribution of values of at least one dimension of the biomolecules in the sample. The size profile may be measured by a detector of an electrophoresis system and sent to a separate computing system or one that is part of the electrophoresis system.

In step 520, a computing device (e.g. computing system 150) compares the first size profile to a plurality of reference size profiles. In one aspect, each reference size profile is measured at a different time of degradation of a reference sample of biomolecules. In another aspect, each reference size profile correlates to a different level of integrity. For example the reference size profiles resulting from method 200 may be used, with the RQI of FIG. 4A being used to determine the RQI value of the sample.

In one embodiment, the first size profile may be compared to another set of reference size profiles as well. This may be done in order to provide an average of levels of integrity from different reference samples.

In an embodiment, the ratios of peaks in a size profile may be used for the comparison. In another embodiment, the comparison may take the form of identifying the size profile on a functional fit that approximates the reference size profiles. Thus, since the functional fit is defined by the reference size profiles, such an identification provides a comparison to the reference size profiles. In yet another embodiment, the comparison may be performed by computing an overlap value between the two profiles, e.g., calculating an area of overlap of two normalized electrophoretic traces.

In step 530, the computing device determines the level of integrity of the sample of biomolecules, based on a similarity of the first size profile to one or more of the reference size profiles. The exact method for determining the level of integrity can be varied. For example, the level of integrity of the reference size profile that is most similar to the first size profile may be used as the level of integrity for the first size profile. The level of integrity of the first size profile may also be taken as an average of the levels of integrity of two or more size profiles that are similar. For example, the first size profile may lie between two reference size profiles, and a weighted average of the levels for those two reference size profiles may be used.

In one embodiment, an interpolation (e.g. weighted linear combination of the RQIs of each of the reference size profiles) may be used. The linear coefficients may be considered as a measure of an overlap (or other type of similarity) of the first size profile to the size profile of a particular reference size profile.

In one aspect, method 500 maps measurements in an N-dimensional space (e.g. fluorescent signal values) into a simplified single dimensional space. As described herein, the simplified expression may be a number (RQI value), color, or other classification. In one embodiment, the RQI value is defined as: $I_S = I_i \alpha_i$, where $I_i$ is a set of integrity numbers assigned to the standards, and where $\alpha_i$ is a measure of similarity (e.g. overlap) of the first size profile to the ith reference size profile.

The underlying physics of the RNA degradation and peculiarities of the signal measurements makes it reasonable to assume that the degradation-related characteristics can be presented as a ratio of the signal values over different intervals. In one aspect, for sample-to-sample compatibility, the intervals should be selected in the vicinity of a distinctive mark related to the molecules of the same size. In one embodiment, Ribsomal RNA (rRNA) peaks are used as the distinctive marks. In this manner, a shifting in time of the electropherogram can be accounted for.

Figure 6:
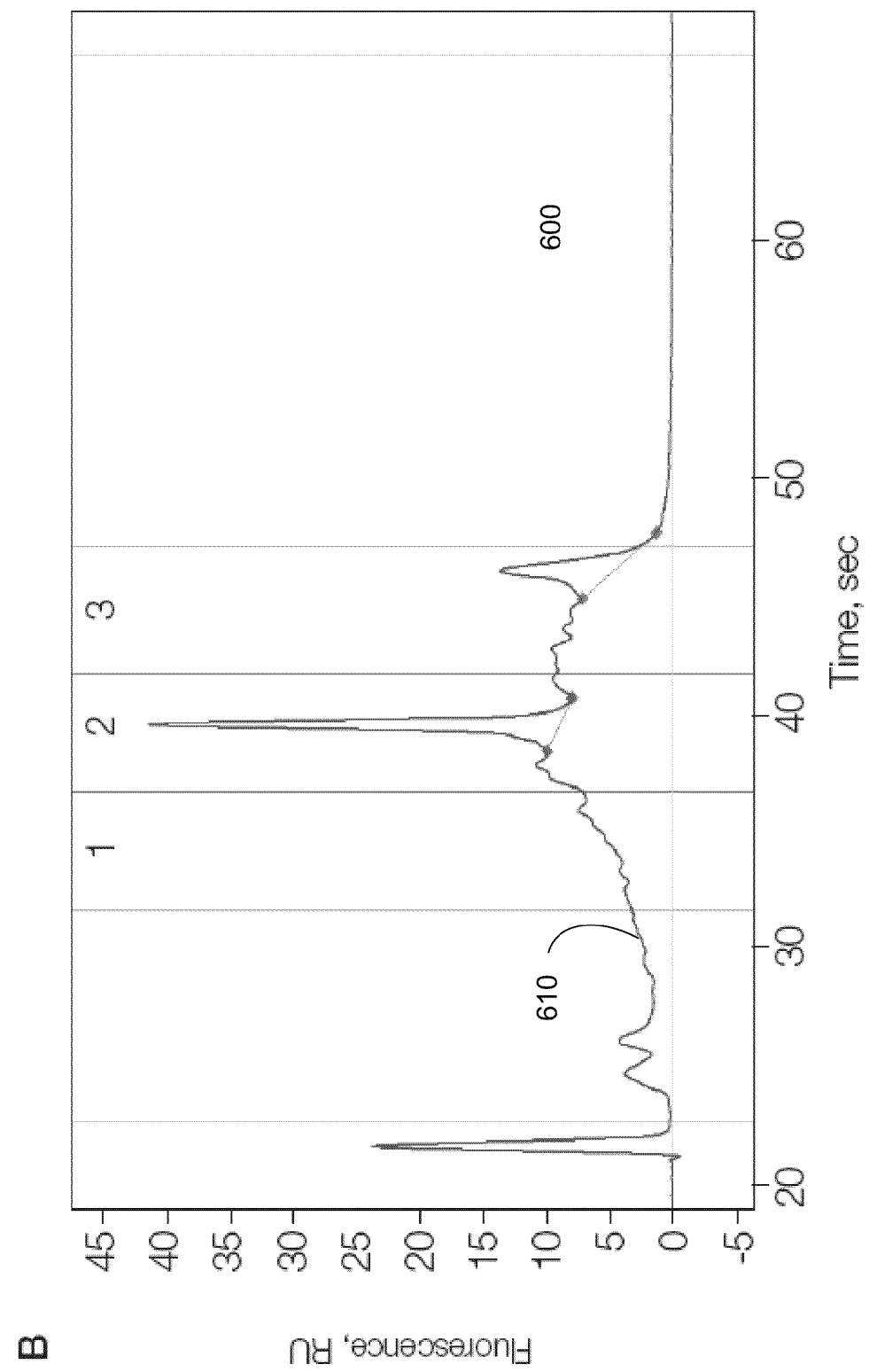
FIG. 6 shows an electropherogram 600 with rRNA peaks and three regions whose area ratios are used to define a size profile according to embodiments of the present invention.

FIG. 6 shows an electropherogram 600 with rRNA peaks and three regions whose area ratios are used to define a size profile according to embodiments of the present invention. As with the electropherogram of FIG. 1B, the Y axis is the fluorescence and the X axis is time in second.

Region 1 relates to a pre-18S peak area, region 2 relates to the 18S peak area, and region 3 relates to the 28S peak area. The different areas are calculated by determining the area under the curve 610 for the width of a particular region. The 28S:18S and 18S:pre-18S ratios, as well as any RNA concentrations may be automatically calculated.

In an embodiment, the 18S peak region and the 28S peak region are defined by the peaks within the respective regions. A user can identify a particular time window or part of the electropherogram in which to search for these peaks. The system software can find the peaks and then locate the regions around the peaks. The final widths may be the same as the time window that the user entered to find the peaks, or the widths may be different. In one embodiment, the pre-18S width is the same as the 18S width. In another embodiment, the start of the 18S region may be determined when the signal reaches a threshold value.

Accordingly, in one embodiment, an area ratio of the ribosomal fragments (e.g. the area ratios of region 3 to 2 and/or the area ratios of region 1 to 2) may be used to define a size profile. For example, a size profile may be defined by these two ratios. These one or more ratios may be what is stored as a reference size profile. These area ratios are examples of size features of a size profile. Other suitable size features, such as peak heights or time location for a peak may be used.

The 28S/18S ratio generally decreases during continued degradation, and the pre-18S/18S ratio generally increases during continued degradation. Thus, each of the different standards will generally have a different ratio (i.e. there is a one to one mapping of the area ration to a standard and an RQI value). Accordingly, these ratios may be used to determine a level of integrity (e.g. an RQI) of a sample.

Figure 7:
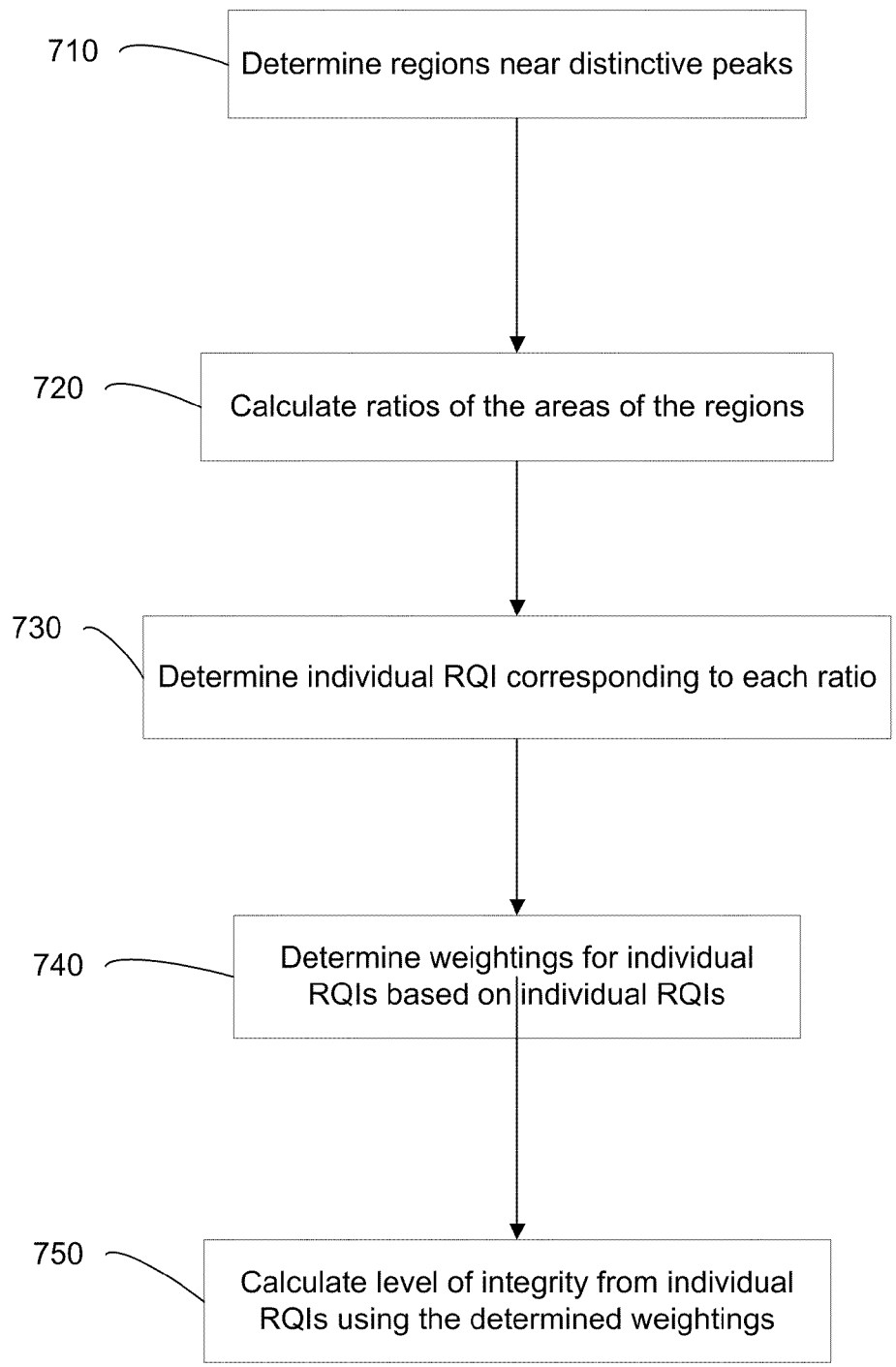
FIG. 7 is a flowchart of a method 700 for determining a level of integrity of a sample of biomolecules using peak area ratios according to embodiments of the present invention.

FIG. 7 is a flowchart of a method 700 for determining a level of integrity of a sample of biomolecules using peak area ratios according to embodiments of the present invention. In one embodiment, method 700 uses the pre-18S/18S ratio and the 28S/18S ratios to define a size profile. In one aspect, method 700 can take 30 minutes from start of a run of the electrophoresis process on the sample to obtaining the level of integrity.

In step 710, regions near a distinctive peak (or other marking) are determined. In one embodiment, three regions are the pre-18S (below the 18S rRNA band), 18S, and 28S regions of an electropherogram, as shown in FIG. 5. The 28S and 18S ribosomal peaks are prominent components of intact RNA, while pre-18S and 18S regions of the electropherogram are prominent components in assessing degraded RNA. In another embodiment, only one of the ratios is used.

In step 720, ratios of the areas of the regions are calculated. In one embodiment, the pre-18S/18S ratio and the 28S/18S ratios are calculated as defining the first size profile of the sample whose level of integrity is to be determined. Note that the inverse of the ratios may also be used. In another embodiment, the areas for each region are normalized by the entire area under the curve.

In one embodiment, a user can directly redefine ribosomal fragments on-screen (i.e. a display of the electropherogram trace). For example, the user can change a fragment start and/or end, thereby causing a change in a position of the region(s) and an area of the region(s). As another example, the user can adjust a width of a region. In another embodiment, the user can adjust peak finding parameters in the software, which can affect the position and area of a region.

In step 730, an individual RQI (integrity value) for each of the ratios is determined for the sample by comparing to the corresponding ratios of a plurality of reference ratios defining a set of reference size profiles. In one embodiment, the pre-18S/18S ratio increases between each reference size profile of a lower integrity, thus this ratio of the sample can be placed between the ratios of two reference size profiles. Thus, the closest standards can define the sample degradation index (i.e. level of integrity of the sample). In one aspect, the sample degradation index may be calculated as a normalized linear interpolation between the two closest standards.

For example, the pre-18S/18S ratio of the first size profile may have a value of 1.5, which lies between values of 1.3 (corresponding to RQI of 8) and 1.7 (corresponding to RQI of 6) of the reference size profiles. Thus, the RQI for the pre-18S/18S ratio of the first size profile may be taken as 7, an equal weighted average of the values (1.3 and 1.7). If the pre-18S/18S ratio was closer to 1.7, the weighted average would favor 6, and the RQI would be less than 7. A similar procedure may be done for a 28S/18S ratio that decreases for reference size profiles of a lower integrity.

In another embodiment, the data points of the pre-18S/18S ratio vs. RQI may be fit to a functional form (e.g. using least squares, interpolation, or any other suitable fitting method). Thus, a specific value of the functional form will map a value of the pre-18S/18S ratio to an RQI value. The functional form may be stored in an electrophoresis system as the reference size profiles. Note when the value of the pre-18S/18S ratio is determined from the functional form, the value from the reference size profiles are still being compared. The 28S/18S ratio may be determined in the same manner.

A level of integrity for the sample is then determined from the individual RQIs of the two ratios for the first size profile. For example, a weighted average may be taken. To determine, such a weighting the following steps may be done.

In step 740, weightings for individual RQIs are determined based on individual RQIs (or equivalently the ratios values when there is a 1-1 mapping). In one embodiment, the weightings are determined based on the relation of the individual RQIs to each other. In another embodiment, the weightings are determined based on the relation of the individual RQIs to an absolute value.

In one embodiment, one of the ratios or equivalently the RQI corresponding to the ratio is compared to a threshold value. For example, the 28S/18S ratio or equivalently the RQI of the 28S/18S ratio is compared to a threshold value. In one embodiment, the threshold of the RQI is 6. Depending on this comparison, different weights are used. The pre-18S/18S ratio may be compared to a threshold instead.

If the RQI of the 28S/18S ratio is greater than the threshold, then the RQI of the 28S/18S ratio has a greater weighting in the average. In one embodiment, the 28S/18S ratio is weighted by a factor three over the pre-18S/18S ratio if the 28S/18S ratio is greater than the threshold. In another embodiment, the 28S/18S ratio and the pre-18S/18S ratio are weighted equally.

Accordingly, in one embodiment, differential weighting is used to evaluate components of the electropherogram, based on how the sample maps to the reference standards. In cases where the RNA sample maps to a more degraded standard, more emphasis is placed on the pre-18S and 18S regions of the electropherogram for generating the RQI value. In other cases where the RNA sample maps to a higher integrity standard, more emphasis is placed on the 28S and 18S regions. The initial determination may be made from the individual RQIs for either of the ratios.

In step 750, level of integrity is calculated from individual RQIs using the determined weightings. For example, an average using the weighting may be used.

In summary, embodiments provide methods and electrophoresis systems that offer a robust assessment of RNA integrity. In one embodiment, three regions of an electrophoretic profile are compared to a series of degradation standards. As shown in the examples section, embodiments are shown to work well over a wide range of RNA concentrations (100 pg to 5,000 ng), is very reproducible (% CV<3), and is applicable to a wide range of mammalian tissues. Also, the applicability has been demonstrated in a report showing a strict correlation between RQI values and RNA quantitation results by real-time PCR.

Accordingly, embodiments can check for RNA degradation using automated separation, detection, and data analysis. Also, embodiments provide a useful tool to quantitatively assess integrity of RNA samples before embarking on labor-intensive and costly projects, and enable the standardization of sample testing for microarray and quantitative real-time PCR analyses. This process, paired with chip priming station and proprietary software, provides improved data generation, storage, and reporting. Additionally, minimal sample requirements mean that a user won't waste a drop of previous samples.

Figure 8:
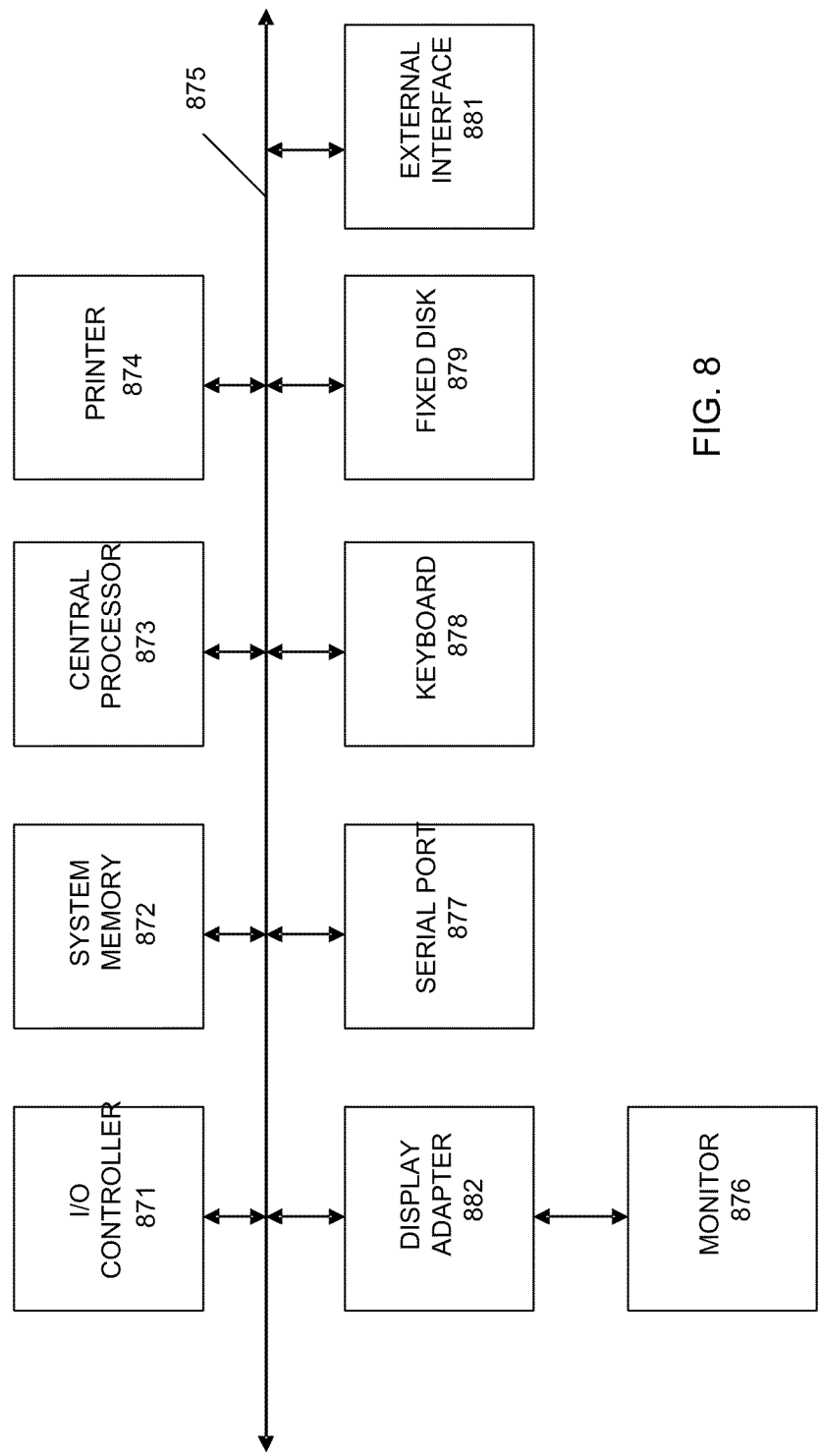
FIG. 8 shows a block diagram of an exemplary computer apparatus usable with system and methods according to embodiments of the present invention.

FIG. 8 shows a block diagram of an exemplary computer apparatus usable with system and methods according to embodiments of the present invention. For example, the computer apparatus is usable as or as part of the computing system 150 of FIG. 1A.

Any of the PLC or computer terminal may utilize any suitable number of subsystems. Examples of such subsystems or components are shown in FIG. 8. The subsystems shown in FIG. 8 are interconnected via a system bus 875. Additional subsystems such as a printer 874, keyboard 878, fixed disk 879, monitor 876, which is coupled to display adapter 882, and others are shown. Peripherals and input/output (I/O) devices, which couple to I/O controller 871, can be connected to the computer system by any number of means known in the art, such as serial port 877. For example, serial port 877 or external interface 881 can be used to connect the computer apparatus to a wide area network such as the Internet, a mouse input device, or a scanner. The interconnection via system bus allows the central processor 873 to communicate with each subsystem and to control the execution of instructions from system memory 872 or the fixed disk 879, as well as the exchange of information between subsystems. The system memory 872 and/or the fixed disk 879 may embody a computer readable medium.

The specific details of the specific aspects of the present invention may be combined in any suitable manner without departing from the spirit and scope of embodiments of the invention. However, other embodiments of the invention may be directed to specific embodiments relating to each individual aspects, or specific combinations of these individual aspects.

It should be understood that the present invention as described above can be implemented in the form of control logic using hardware and/or using computer software in a modular or integrated manner. Based on the disclosure and teachings provided herein, a person of ordinary skill in the art will know and appreciate other ways and/or methods to implement the present invention using hardware and a combination of hardware and software Any of the software components or functions described in this application, may be implemented as software code to be executed by a processor using any suitable computer language such as, for example, C#, Java, C++ or Perl using, for example, conventional or object-oriented techniques. The software code may be stored as a series of instructions, or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive or an entire computer system), and may be present on or within different computer program products within a system or network. A computer system may include a monitor, printer, or other suitable display for providing any of the results mentioned herein to a user.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

EXAMPLES

The following examples are offered to illustrate, but not to limit the claimed invention.

I. Reproducibility

Interchip reproducibility of RQI values was evaluated by analyzing a mouse brain total RNA sample (Ambion) at 250 ng/jJl on six different chips with 12 samples per chip (n=72). The RQI values returned ranged between 8.7 and 9.7 with a mean RQI value of 9.4 and a percent coefficient of variation (% CV) of 3.5%. Reproducibility of RQI measurements on a less intact sample of rat liver RNA run at two different concentrations, 100 ng/jJl and 2 ng/jJl, showed a high reproducibility across 12 and 11 runs using the Experion RNA 8td8ens and High8ens analysis chips, respectively. All RQI values fell into a tight range with a low standard deviation, as shown in Table 1 of FIG. 9A. Together, these data show that RQI values are very reproducible.

II. Effect of Concentration

The effect of RNA concentration on RQI precision was determined by analyzing RNA samples with different levels of integrity. RNA samples were diluted to cover the entire dynamic range of the standard and high-sensitivity RNA chips. The qualitative detection range is 5-500 ng/fJl and 100-5,000 pg/fJl for Experion RNA StdSens and HighSens chips, respectively, as shown in Table 2 of FIG. 9B.

Figure 10:
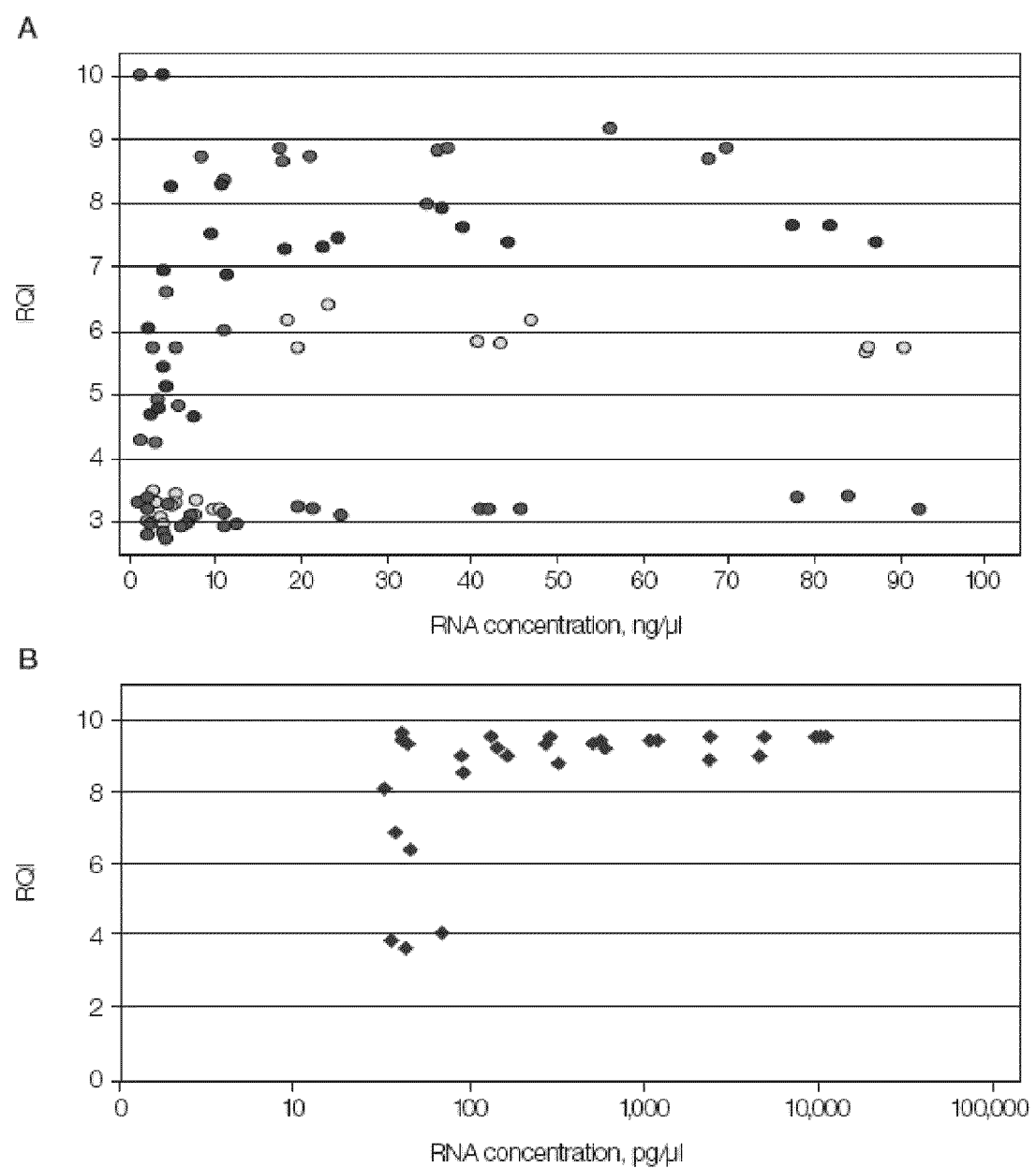
FIGS. 10A and 10B show the effect of RNA concentration on RQI determination according to an embodiment of the present invention.

FIGS. 10A and 10B show the effect of RNA concentration on RQI determination according to an embodiment of the present invention. To determine the lower limit of RNA concentrations for RQI determination using the Experion RNA StdSens chip, four samples of RNA from mouse and rat liver with different levels of integrity (RQI values ranging between −3 and 9, FIGS. 10A, B) were used. Twelve serial dilutions (between 1-100 ng/µl) were prepared from each sample and run in triplicate on three StdSens analysis chips. The reported RQI values at each concentration, as measured by the Experion system (FIG. 10A), indicate that a correct RQI value (within 1 unit of its expected value) is returned for RNA concentrations above 10 ng/µl.

The lower limit of RNA concentrations for RQI determination with the HighSens analysis chip was determined using an intact mouse liver RNA sample. Twelve RNA concentrations ranging between 10-10,000 pg/µl were analyzed in triplicate using HighSens analysis chips, The results (FIG. 10B) indicate that the RQI value is accurately reported (within 1 unit of its expected value) above 200 pg/µl with the Experion RNA HighSens analysis chip.

These experiments showed that a reliable RQI value is reported at or below the actual lower limit of quantitative detection for RNA for both Experion RNA chips (Table 2 of FIG. 9B). For samples whose concentrations fall below these thresholds, the Experion system cannot reliably report a valid RQI value and conveniently flags the sample by providing the comment "RNA conc. too low". This cutoff can be overridden by the user by checking a box in the RQI settings, allowing display of the values in brackets.

III. Application to Different Tissue and Organism

Embodiments have established reference size profiles using human liver RNA samples for standards and are intended to be used on eukaryotic samples. To test the applicability of the embodiments to different RNA sample types, a variety of different sample tissues and sources were evaluated. These included a series of 20 human RNA samples from different tissues (FirstChoice human total RNA survey panel, Ambion). This study indicated that the RQI method can be used to assess integrity of RNA from a variety of human tissues and compared to measured RIN values. Additionally, hundreds of RNA samples were extracted and RQI values measured for a variety of tissues and organisms, including mouse liver, heart, brain, skin, cartilage, and skeletal muscle; rat brain and liver; rabbit lung; human neural blastoma biopsy samples; human endometrium biopsy samples; and HeLa, Jurkat, and HEPG2 cultured cells. All RQI values, independent of the methods used for RNA extraction (TRI reagent or membrane-based methods, such as Bio-Rad's Aurum total RNA fatty and fibrous tissue kit or Aurum total RNA mini kit), could be confirmed by visual interpretation of the electropherograms.

Although embodiments of reference size profiles created in one tissue and organisms have been shown to be applicable in a variety of tissues and organisms, different standards (reference size profiles) may be used for different tissues and for same tissue but different organism.

IV. Accuracy for RNase Degradation

The RQI algorithm was established using heat-degraded RNA as reference samples. However, degradations that occur during the RNA extraction procedure are generally caused by the action of endogenous or exogenous RNases. To assess the validity of the RQI algorithm on such samples, RQI measurements of heat- and RNase-degraded RNA samples were compared. Endogenous RNase degradation was induced by incubating tissues (liver) at room temperature prior to RNA extraction. The two types of degradations yielded significantly different electrophoresis profiles as shown in FIG. 11.

Figure 11:
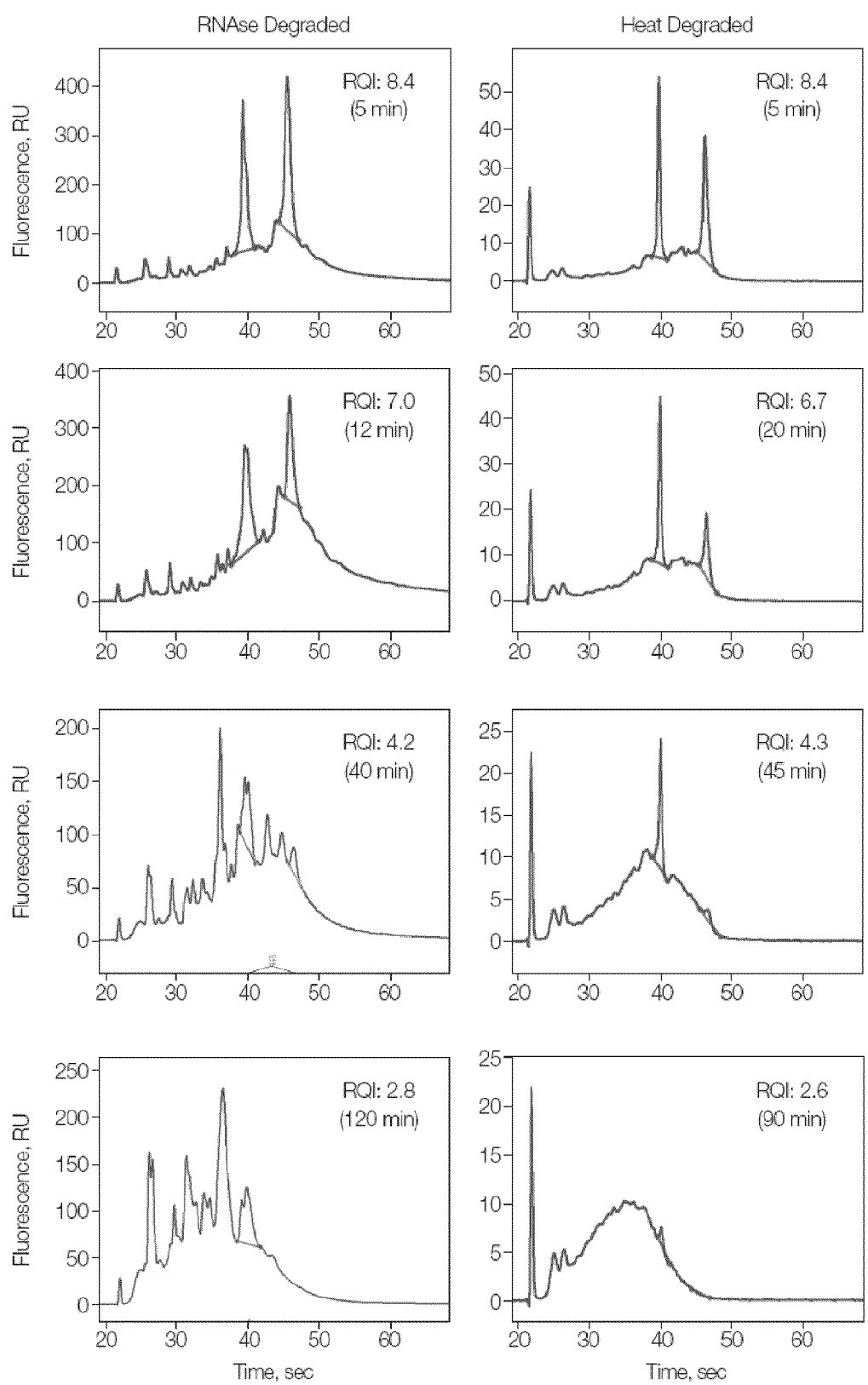
FIG. 11 shows a comparison of electropherogram profiles and RQI values at different time points between natural RNase and heat-mediated degradations according to an embodiment of the present invention.

FIG. 11 shows a comparison of electropherogram profiles and RQI values at different time points between natural RNase and heat-mediated degradations according to an embodiment of the present invention. RNA extracted from rat livers incubated at room temperature prior to extraction (left panels) are compared to profiles from heat-degraded RNAs (right panels). 18S and 28S rRNA peaks map at 40 sec and 47 sec respectively. RQI value and incubation time is indicated for each graph.

One of the main differences resides in the size distribution of the degradation products. While heat degradation produces a homogenous population of fragments across all sizes, degradation by RNases yields fragments of discrete sizes that appear as distinct peaks or spikes in the electropherogram. RQI calculations are not affected by the presence of the discrete bands of degraded RNAs in the pre-18S region of the electropherogram. The RQI software will return a valid number assuming that both the 18S and 28S rRNA peaks have been correctly identified. FIG. 11 shows that similar RQI values, compared to heatdegraded samples, were calculated across a wide range of "natural" degradation times (0-120 min).

V. Raw Accuracy

In a study of over 2,500 RNA samples, less than 1% of the lanes (22 out of 2,500) returned anomalous RQI results (>1 RQI unit different from value expected from visual inspection). Of that small percentage, the most frequent miscalled RQI value occurred due to miscalled ladder lanes, where RNA ladder fragments were misidentified by the software resulting in misidentification of the 18S and 28S regions. Since embodiments of the RQI calculation rely on these regions, their improper identification can lead to erroneous RQI values. This problem can be easily detected by visual inspection of the electropherogram and fixed by adjusting the peak identification parameters or by using manual integration (for the ladder well only) to add or delete ladder peaks to correct the miscalled band. Contamination with DNA may also affect the RQI readings. In rare cases, the peak of contaminating DNA may be identified as the 18S rRNA peak leading to an erroneous RQI value. This too can be corrected by redefining manually where the appropriate fragment starts and ends.

VI. Confirmation with qPCR

Real-time qPCR was performed on liver carcinoma RNA samples that were degraded for different lengths of time by incubation at 90° C. Mean CT values of five transcripts obtained from triplicate reactions were determined at a threshold of 100 relative fluorescence units (RFU) using the iCycler IQ real-time PCR detection system with version 3.1 software. ΔCT indicates the change in CT value over the 7 hr degradation period. Traces for the qPCR reactions from which these data were derived are shown in FIG. 12.

RNA (500 ng) was converted to cDNA using the iScripiM cDNA synthesis kit. The cDNA (10 ng) was then amplified in triplicate reactions with iQ® SYBR® Green supermix, and 0.5 uM of each primer pair for 18S rRNA, and the B-actin, GAPDH, HPRT, or B-tubulin genes using the iCycler iQ® real-time PCR detection system with version 3.1 software (Gingrich et al. 2006).

To determine the amount of RNA degradation in samples at different time points, qPCR was performed on the RNA samples. In these experiments, primers specific for the 18S rRNA and four selected protein-encoding genes were used in real-time qPCR reactions to quantitate the relative abundance of their respective transcripts at the various time points.

Figure 12:
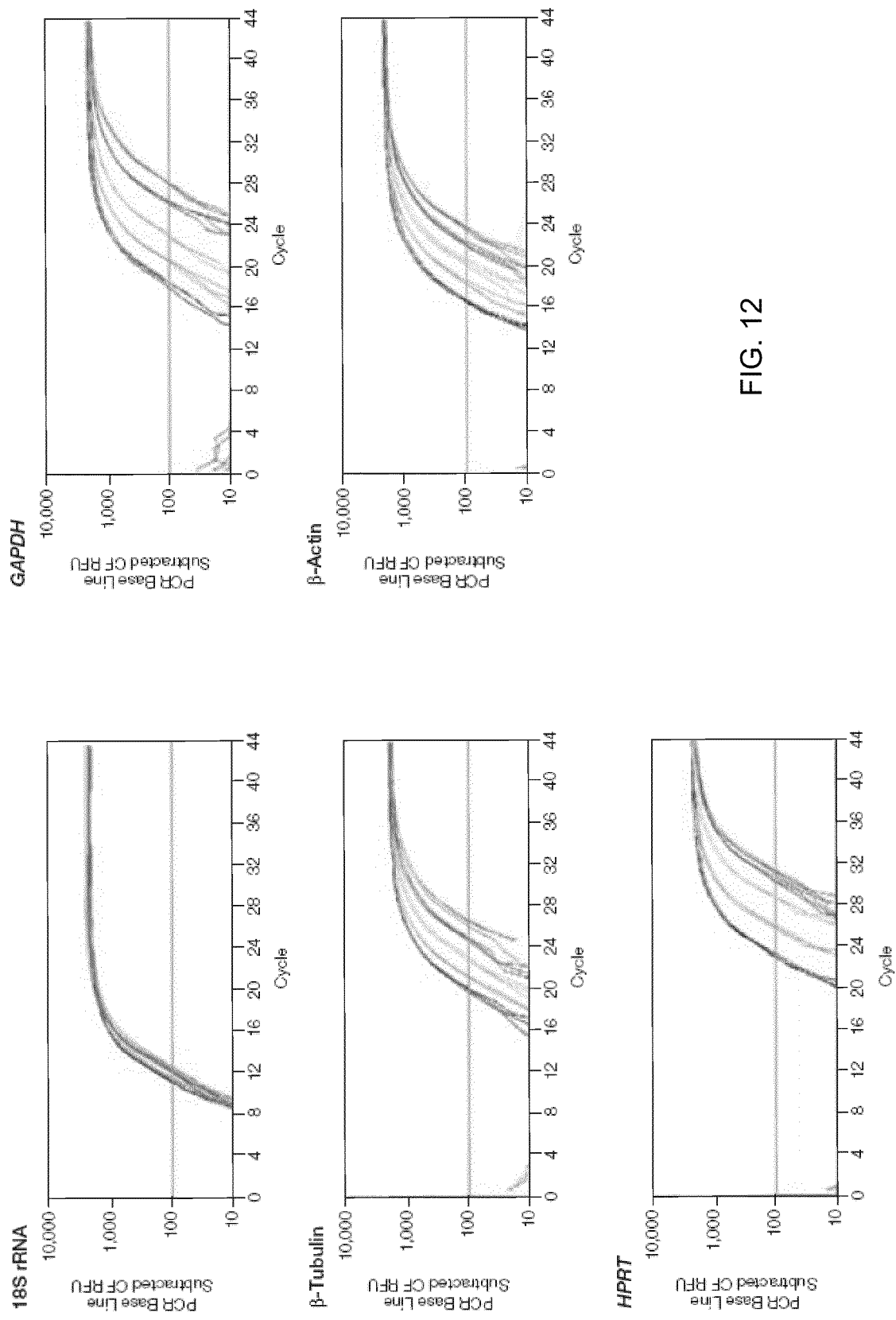
FIG. 12 shows plots illustrating an assessment of RNA degradation by real-time qPCR according to an embodiment of the present invention.

FIG. 12 shows plots illustrating an assessment of RNA degradation by real-time qPCR according to an embodiment of the present invention. qPCR traces obtained from liver carcinoma total RNA samples degraded for different lengths of time and amplified using primers for the genes indicated. As one moves to the right, the different curves are for no degradation; 1 hr degradation; 3 hr degradation; 5 hr degradation; and 7 hr degradation. Mean CT values obtained from these traces are shown in Table 3 of FIG. 9C.

The results presented in FIG. 12 show that while 18S rRNA appears to have remained mostly intact over the degradation time course, the abundance of the transcripts of the four protein-encoding genes decreased over time.

Degradation rates for the protein-encoding gene transcripts are reflected in the increasing threshold cycle (CT). In real-time qPCR experiments, the CT number is the number of cycles needed for amplified cDNA fluorescence to pass a set threshold. The CT number is used to compare the difference in quantity of starting transcript. A difference of one cycle reflects a 2-fold difference in the amount of starting transcript (assuming 100% amplification efficiency).

The CT values of the qPCR reactions from the five gene transcripts are shown in Table 3 of FIG. 9C. The data indicate that the transcripts of the four protein-encoding genes tested were present in different amounts in the initial sample with the B-actin transcript being the most abundant and HPRT transcript the least abundant. As expected, transcripts of the 18S rRNA were much more abundant than any of the protein coding gene transcripts. Through the 7 hr degradation time, the 18S rRNA was degraded to a much lesser extent than the protein gene transcripts, as seen by a ΔCT of 1.3, representing a 2.5-fold ($2^{1.3}$) decrease in transcript amount compared to the protein gene transcripts with a ΔCT of 6.8 to 9.9, representing a 128 to 1, ODD-fold (26.8 to 29.9) decrease in transcript abundance.

Figure 13:
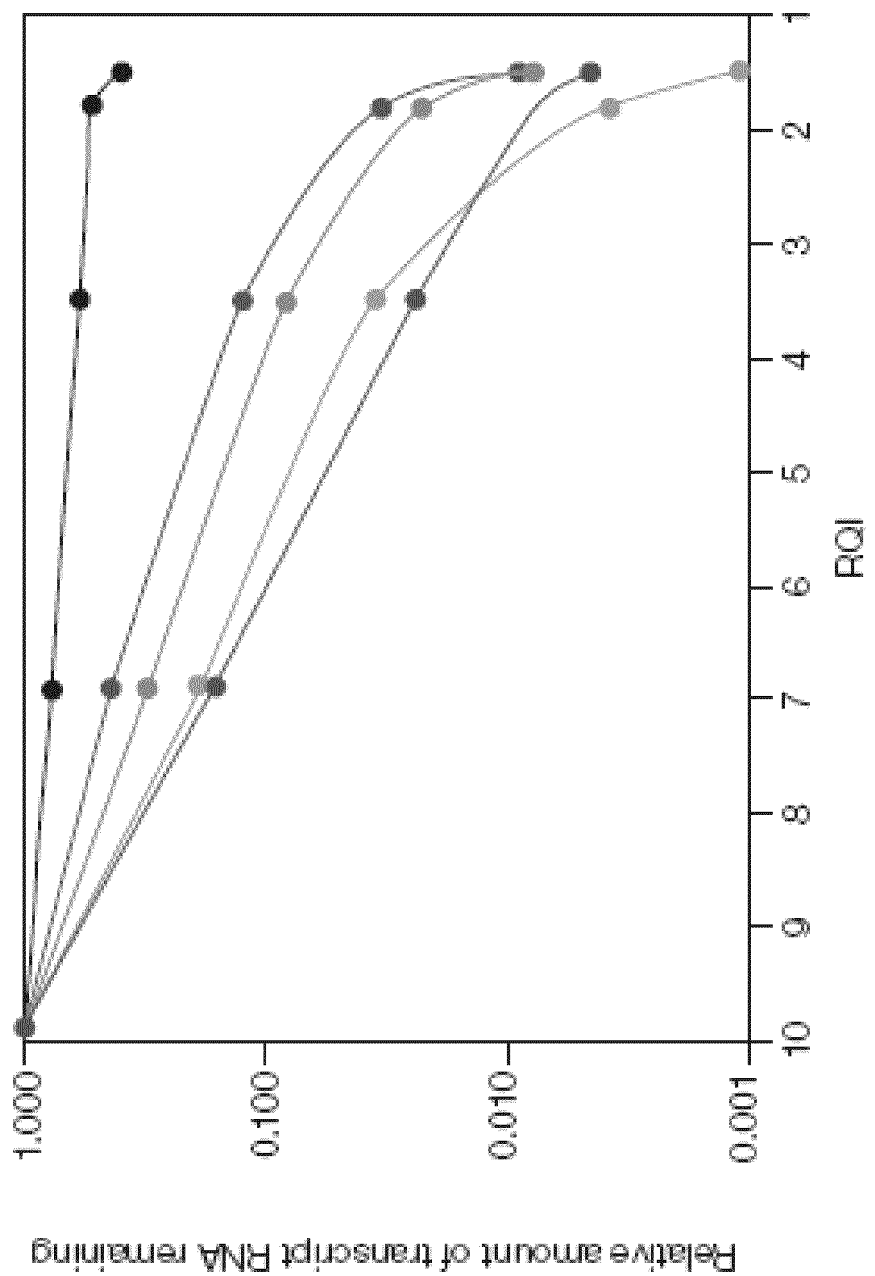
FIG. 13 is a plot illustrating a correlation between RQI and the relative amount of specific transcript RNA remaining according to an embodiment of the present invention.

In order to correlate the relative amount of remaining RNA of the five different gene transcripts with the measured RQI of the RNA samples, values were plotted as shown in FIG. 13. An arbitrary value of 1 was assigned to the transcript levels corresponding to an RQI of 10. All other values were calculated from the CT values shown in Table 3, assuming that the number of transcripts is reduced by a factor of 2 for each CT increase of 1.

The plot of FIG. 13 shows that the transcript levels for all five genes decrease logarithmically relative to the RQI measurements down to an RQI value of 3. Below this value, the transcripts decrease at a much faster rate. As mentioned previously, the 18S rRNA transcripts were more abundant and less affected by degradation. The rates of decrease of the four protein-encoding transcripts relative to their RQI measurements were quite similar. Transcripts for HPRT and GAPDH disappeared slightly faster than those for B-actin and B-tubulin. For example, the transcripts for HPRT decreased 10-fold over an RQI range of 4 units, while the transcripts for B-tubulin decreased 10-fold over an RQI range of 7 units.

These results demonstrate that RQI measurements can be used to estimate the degree of degradation in an RNA sample. Although we looked at only four protein-encoding genes, they all appeared to degrade to different extents relative to the RQI score. This indicates that one may re-evaluate RNA degradation states when comparing or performing qPCR to ensure reliable results. For example, the color coding may change or the RQI values may change depending on what specific biomolecule of interest is being used (e.g. amplified). Regardless though, the RQI still provides a consistent value for a particular degradation state. It is up to the researcher of a specific technique to identify which RQI values are required for a specific experiment.

Therefore, embodiments have been shown to determine a level of integrity (e.g. the RQI value) with an efficient method that takes into account only three regions of the electropherogram and that has been shown to be accurate.

What is claimed is:

1. A method of improving accuracy and reproducibility of determining a level of integrity of a sample of ribonucleic acid (RNA) and/or deoxyribonucleic acid (DNA) molecules, the method comprising:

receiving a first size profile of the sample of the RNA and/or DNA molecules, wherein a size profile provides a measure of a distribution of values of at least one dimension of the RNA and/or DNA molecules, in the sample, the at least one dimension including length and/or weight;

comparing, with an electrophoresis system, the first size profile to a plurality of reference size profiles, wherein each reference size profile correlates to a different level of integrity; and based on a similarity of the first size profile to one or more of the reference size profiles, determining, with the electrophoresis system, the level of integrity of the sample of RNA and/or DNA molecules, wherein the plurality of reference size profiles is obtained by:

at each of a plurality of different elapsed times relative to an initial time:

measuring a respective reference size profile of a reference sample of RNA and/or DNA molecules selected from a group of reference samples having about the same initial integrity, wherein each respective reference size profile corresponds to a different amount of degradation of the reference sample, wherein each reference size profile provides a measure of a distribution of values of the at least one dimension of the RNA and/or DNA molecules in the reference sample; and mapping each reference size profile to a level of integrity, a highest integrity level of reference size profile being measured at the initial time, and each successive lower integrity level of reference size profile being measured at a longer elapsed time from the initial time.

2. The method of claim 1, wherein the reference size profiles are derived from one or more reference samples containing RNA and/or DNA molecules of the same origin and the same concentration.

3. The method of claim 1, wherein the level of integrity is expressed as a numerical value within predetermined scale.

4. The method of claim 1, wherein the different elapsed times of degradation of the reference size profiles are zero and successive periodic times.

5. The method of claim 1, wherein the reference size profiles map linearly to different levels of integrity.

6. The method of claim 1, wherein a size profile comprises a plurality of ratios of at least three regions, wherein each region corresponds to a different amount of time for RNA and/or DNA molecules of the sample to reach a detection point, wherein RNA and/or DNA molecules of different size reach the detection point at different times.

7. The method of claim 6, wherein the comparing includes:
comparing one or more size features of the first size profile to corresponding size features of the reference size profiles,
wherein determining the level of integrity of the sample of RNA and/or DNA molecules includes:
based on the comparing, determining an integrity value for each size feature of the first size profile; and
averaging the integrity values to determine the level of integrity of the sample of RNA and/or DNA molecules.

8. The method of claim 7, wherein the one or more size features include a ratio of areas of a size profile around the rRNA peaks of 18S and 28S.

9. The method of claim 7, wherein averaging weights one size feature higher if the integrity value of the one size feature is higher than a threshold value.

10. The method of claim 7, wherein for each size feature of the first size profile:
comparing one or more size features of the first size profile to corresponding size features of the reference size profiles includes:
identifying two reference profiles having corresponding size features with values between which lies the value for the respective size feature of the first size profile; and
calculating the differences between the respective size feature of the first size profile and the values of the corresponding size features of the two reference profiles, and
determining an integrity value includes:
interpolating between the values of the corresponding size features of the two reference size profiles to determine the integrity value of the respective size feature.

11. The method of claim 1, wherein the size profile is an electropherogram.

12. A computer program product comprising a non-transitory computer readable medium storing a plurality of instructions for controlling a processor to perform an operation for of determining a level of integrity of a sample of ribonucleic acid (RNA) and/or deoxyribonucleic acid (DNA) molecules, the instructions comprising:

receiving a first size profile of the sample of the RNA and/or DNA molecules, wherein a size profile provides a measure of a distribution of values of at least one dimension of the RNA and/or DNA molecules in the sample, the at least one dimension including length and/or weight;

comparing the first size profile to a plurality of reference size profiles, wherein each reference size profile correlates to a different level of integrity; and based on a similarity of the first size profile to one or more of the reference size profiles, determining the level of integrity of the sample of RNA and/or DNA molecules, wherein the plurality of reference size profiles is obtained by:

at each of a plurality of different elapsed times relative to an initial time:
measuring a respective reference size profile of a reference sample of RNA and/or DNA molecules selected from a group of reference samples having about the same initial integrity, wherein each respective reference size profile corresponds to a different amount of degradation of the reference sample, wherein each reference size profile provides a measure of a distribution of values of the at least one dimension of the RNA and/or DNA molecules in the reference sample; and mapping each reference size profile to a level of integrity, a highest integrity level of reference size profile being measured at the initial time, and each successive lower integrity level of reference size profile being measured at a longer elapsed time from the initial time.

13. An electrophoresis system comprising:
a voltage source;
a detector;
the computer program product of claim 12; and
one or more processors communicably coupled with the detector and the computer program product.

14. The electrophoresis system of claim 13, wherein the computer program product stores the reference size profiles.

15. The electrophoresis system of claim 13, further comprising a light source that excites luminescent markers on the biomolecules, the light source illuminating a first electromagnetic radiation at a detection point, and wherein the detector detects a second electromagnetic radiation emitted from the excited biomolecules at the detection point at a specific instance in time.

16. A method of deriving reference size profiles for an electrophoresis system, the method comprising:
receiving a reference sample of biomolecules;
at each of a plurality of different elapsed times relative to an initial time:
measuring, with an electrophoresis system, a respective size profile of the reference sample of biomolecules, wherein a size profile provides a measure of a distribution of values of at least one dimension of the biomolecules in the reference sample,
wherein each respective size profile corresponds to a different amount of degradation of the reference sample; and
mapping each size profile to a level of integrity, wherein a size profile measured at a later elapsed time maps to a lower level of integrity.

17. The method of claim 16, further comprising:
storing, in a computer readable medium of the electrophoresis system, the size profiles associated with the corresponding level of integrity.

18. The method of claim 16, wherein the reference sample has no degradation prior to the measurement of a first size profile at the initial time.

19. The method of claim 16, wherein the mapping is non-linear.

20. The method of claim 16, further comprising:
degrading the reference sample at the plurality of elapsed times by subjecting the reference sample to heat.

21. The method of claim 17, further comprising:
repeating for one or more additional reference samples, each selected from a group of reference samples having about the same initial integrity; and
taking an average of the size profiles taken at each elapsed time, wherein the average of the size profiles is stored in the computer readable medium.

22. The method of claim 16, wherein the plurality of different elapsed times are predetermined, and wherein a respective size profile is measured when a predetermined elapsed times is reached.

* * * * *